(12) United States Patent
Jin et al.

(10) Patent No.: US 7,119,209 B2
(45) Date of Patent: Oct. 10, 2006

(54) PROCESS FOR PREPARING INDOLINONE DERIVATIVES

(75) Inventors: Qingwu Jin, Kalamazoo, MI (US); Michael A. Mauragis, Scotts, MI (US); Paul D. May, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 458 days.

(21) Appl. No.: 10/367,008

(22) Filed: Feb. 14, 2003

(65) Prior Publication Data

US 2003/0229229 A1 Dec. 11, 2003

Related U.S. Application Data

(63) Continuation-in-part of application No. PCT/US02/04407, filed on Feb. 15, 2002.
(60) Provisional application No. 60/411,732, filed on Sep. 18, 2002.

(51) Int. Cl.
*C07D 417/06* (2006.01)
*C07D 249/08* (2006.01)
*C07D 403/02* (2006.01)
*C07D 209/04* (2006.01)

(52) U.S. Cl. .................... 548/181; 548/236; 548/266.2; 548/312.1; 548/468

(58) Field of Classification Search ................ 548/181, 548/236, 266.2, 312.1, 468; 544/144
See application file for complete search history.

(56) References Cited

U.S. PATENT DOCUMENTS

| 6,133,305 A | 10/2000 | Tang et al. | 514/418 |
|---|---|---|---|
| 6,248,771 B1 | 6/2001 | Shenoy et al. | 514/418 |
| 6,316,429 B1 | 11/2001 | Tang et al. | 514/80 |
| 6,316,635 B1 | 11/2001 | Tang et al. | 548/312.1 |
| 6,653,308 B1 * | 11/2003 | Guan et al. | 514/235.2 |

FOREIGN PATENT DOCUMENTS

| WO | WO 99/48868 | 9/1999 |
|---|---|---|
| WO | WO 01/45689 | 6/2001 |
| WO | WO 01/60814 | 8/2001 |
| WO | WO 02/066463 | 8/2002 |
| WO | WO 03/035009 | 5/2003 |

OTHER PUBLICATIONS

Oussaid, B. et al., "Thiophene–Containing Macrocycles Derived from (2+2) Cyclizations", Phosphorus, Sulfur, and Silicon, vol. 73, 1992, 41–47, XP009012169.

Reddy, K.P. et al., "Synthesis and Mesomorphic Behaviour of a Homologous Series of 1,1'–bs(4(4'–alkyloxy) benzaldimine)Ferrocene dicarbosylates" Liquid Crystal, Taylor and Francis Ltd, London, GB, vol. 12, No. 3, Sep. 1, 1992, 369–376, XP000295512.

Staab, H. A. et al, "Azolides in Organic Synthesis and Biochemist" 1998, Wiley–VCH, Weinheim XP002244374, 14–16.

* cited by examiner

*Primary Examiner*—Johann Richter
*Assistant Examiner*—Ebenezer Sackey
(74) *Attorney, Agent, or Firm*—Peter Richardson; Bryan C. Zielinski; Stephen D. Prodnuk

(57) ABSTRACT

The present invention refers to a process for preparing indolinone derivatives of the general formula (VI) as defined in the specification and intermediates of that process.

43 Claims, No Drawings

US 7,119,209 B2

PROCESS FOR PREPARING INDOLINONE DERIVATIVES

CROSS REFERENCE TO RELATED APPLICATIONS

This patent application claims the benefit of the following provisional application: U.S. Ser. No. 60/411,732, filed Sep. 18, 2002; and is a continuation-in-part of International Application No: PCT/US02/04407, filed Feb. 15, 2002, under 35 USC 119(e)(i), the entire content of both applications being incorporated herein by reference.

FIELD OF THE INVENTION

The present invention refers to a process for preparing indolinone derivatives and intermediates of that process.

BACKGROUND OF THE INVENTION

A number of indolinone derivatives have been found to exhibit pharmaceutical activity. Due to the ability to modulate the protein kinase activity, they have been suggested to treat an number of conditions such as various types of cancer, mastocytosis, allergy associated chronic rhinitis, diabetes, autoimmune disorders, restenosis, fibrosis, psoriasis, von Hippel-Lindau disease, osteoarthritis, rheumatoid arthritis, angiogensis, inflammatory disorders, immunological disorders, and cardiovascular disorders (WO 01/45689, WO 01/60814, WO 99/48868, U.S. Pat. No. 6,316,429, U.S. Pat. Nos. 6,316,635, 6,133,305, and U.S. Pat. No. 6,248,771).

Among the indolinone derivatives those having an amide group on a heterocyclic ring condensed with the indolinone have been of interest. These compounds modulate protein kinase activity and are thus useful in treating diseases relating to abnormal protein kinase activity. A process for preparing the amide derivatives is disclosed in WO 01/60814. An appropriate pyrrole is formylated and subsequently condensed with a 2-indolinone to give a respective 5-(2-oxo-1,2-dihydroindole-3-ylidenemethyl)-1H-pyrrole. If an amide derivative of the pyrrole is desired, a pyrrole having a carboxylic acid group is selected. The carboxylic acid group is reacted with the desired amine in the presence of dimethylformamide, 1-ethyl-3-(3-dimethylamino-propyl) carbodiimide and 1-hydroxybenzotriazole. In example 129 a scale-up procedure is disclosed in which the amidation is conducted in the presence of dimethylformamide, benzotriazole-1-yloxytris(dimethylamino)phosphonium hexafluorophosphate (BOP) and triethylamine.

It is an object of the present invention to provide an improved process for preparing indolinone derivatives which have an amide group on a heterocyclic ring condensed with the indolinone.

SUMMARY OF THE INVENTION

The present invention provides a process for preparing an indolinone of the general formula (VI)

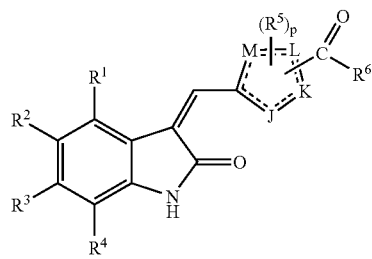

(VI)

wherein
R$^1$, R$^2$, R$^3$, R$^4$ are independently selected from the group consisting of hydrogen, C$_{1-12}$ alkyl, C$_{1-12}$ alkoxy, C$_{5-12}$ cycloalkyl, C$_{6-12}$ aryl, C$_{5-12}$ heterocyclic group containing 1 to 3 atoms selected from N, S or O, provided that the heterocyclic group may be partially unsaturated, but not aromatic, C$_{6-12}$ aryloxy, C$_{6-12}$ alkaryl, C$_{6-12}$ alkaryloxy, halogen, trihalomethyl, hydroxy, —S(O)R', —SO$_2$NR'R", SO$_3$R', —SR', —NO$_2$, —NR'R", —OH, —CN, —C(O)R', —OC(O)R', —NHC(O)R', —(CH$_2$)$_n$CO$_2$R', and —CONR'R";
each R$^5$ is independently selected from the group consisting of hydrogen, C$_{1-12}$ alkyl, C$_{1-12}$ alkoxy, C$_{5-12}$ cycloalkyl, C$_{6-12}$ aryl, C$_{5-12}$ heterocyclic group containing 1 to 3 atoms selected from N, S or O, provided that the heterocyclic group may be partially unsaturated, but not aromatic, C$_{6-12}$ aryloxy, C$_{6-12}$ alkaryl, C$_{6-12}$ alkaryloxy, halogen, trihalomethyl, hydroxy, —S(O)R', —SO$_2$NR'R", —SO$_3$R', —SR', —NO$_2$, —NR'R", —OH, —CN, —C(O)R', —OC(O)R', —NHC(O)R', —(CH$_2$)$_n$CO$_2$R', and —CONR'R"; R$^6$ is selected from —NR$^8$(CH$_2$)$_m$R$^9$ and —NR$^{10}$R$^{11}$, provided that optionally one to two of the CH$_2$ groups may be substituted by —OH or halogen; R$^8$ is hydrogen or C$_{1-12}$ alkyl;
R$^9$ is selected from the group consisting of —NR$^{10}$R$^{11}$, —OH, —C(O)R$^{12}$, C$_{6-12}$ aryl, C$_{5-12}$ heterocyclic group containing 1 to 3 atoms selected from N, S or O, —N$^+$(O$^-$)R$^{10}$, and —NHC(O)R$^{13}$;
R$^{10}$ and R$^{11}$ are independently selected from the group consisting of hydrogen, C$_{1-12}$ alkyl, C$_{1-12}$ cyanoalkyl, C$_{5-12}$ cycloalkyl, C$_{6-12}$ aryl, and C$_{5-12}$ heterocyclic group containing 1 to 3 atoms selected from N, S or O; or R$^{10}$ and R$^{11}$ may be combined to form a five- or six-membered heterocyclic group optionally containing 1 to 3 atoms selected from N, O, or S in addition to the nitrogen atom to which R$^{10}$ and R$^{11}$ are bound, provided that the heterocyclic group formed by R$^{10}$ and R$^{11}$ may optionally be substituted by R'
R$^{12}$ is selected from the group consisting of hydrogen, —OH, C$_{1-12}$ alkoxy and C$_{6-12}$ aryloxy;
R$^{13}$ is selected from the group consisting of C$_{1-12}$ alkyl, C$_{1-12}$ haloalkyl, and C$_{6-12}$ aralkyl;
R' and R" are independently selected from the group consisting of hydrogen, C$_{1-12}$ alkyl, C$_{1-12}$ cyanoalkyl, C$_{5-12}$ cycloalkyl, C$_{6-12}$ aryl, C$_{5-12}$ heterocyclic group containing 1 to 3 atoms selected from N, S or O, provided that the heterocyclic group may be partially unsaturated, but not aromatic, or in the group —NR'R" the R' and R" substituents may be combined to form a five- or six-membered heterocyclic group optionally containing 1 to 3 atoms selected from N, O, or S in addition to the nitrogen atom to which R' and R" are bound,
The terms "halogen" and "halo" refer to substituents selected from the group consisting of F, Cl, Br, and I
J is selected from the group consisting of O, S, and NH;

one of K, L and M is C and the group —C(O)R$^6$ is bound thereto, the others of the group of K, L and M are independently selected from the group consisting of CR$^5$, CR$^5{}_2$, N, NR$^5$, O and S;

n is 0, 1 or 2;

m is 1, 2, 3, or 4; and p is 0, 1 or 2;

comprising the steps of (i) reacting a compound of general formula (I)

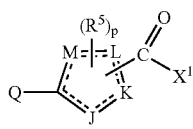

Formula I wherein R$^5$, J, K, L, M and p are as defined above, Q is selected from the group consisting of

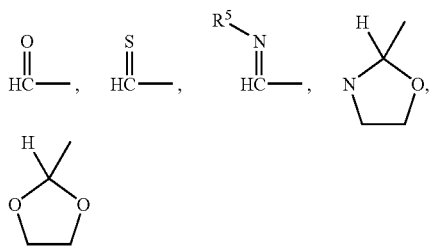

with a compound of general formula (II)

X$^2$—R  (II)

wherein:

(a) one of X$^1$ and X$^2$ is chlorine, or bromine, and the other is selected from the group consisting of hydroxy, —O—C$_{1-4}$ alkyl and —O-phenyl, and R is selected from the group consisting of —C(O)—C$_{1-4}$ alkyl, C(O)—O—(C$_{1-4}$)alkyl, —C(O)—O-phenyl, provided that the phenyl may optionally be substituted by 1 to 3 halogen atoms, —C(O)—O—CH$_2$-phenyl, provided that the phenyl may optionally be substituted by 1 to 3 halogen atoms, or (b) X$^1$ is chlorine or bromine, X$^2$ is hydrogen and R is selected from the group consisting of

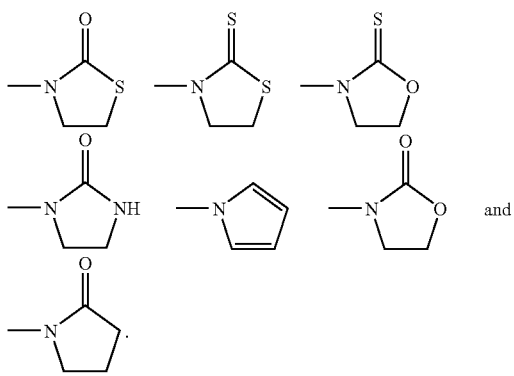

and or (c) X$^1$ is hydroxy, —O—C$_{1-4}$ alkyl and —O-phenyl, X$^2$ is

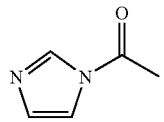

and R is

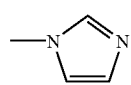

to form a compound of the general formula (III)

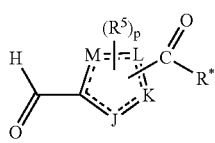

(III)

wherein R* is —O—R in case (a) of step (i) and —R in cases (b) and (c) of step (i), (ii) reacting the compound of general formula (III) with a compound of general formula (IV)

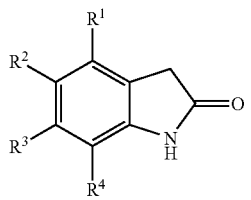

(IV)

wherein R$^1$, R$^2$, R$^3$, and R$^4$ are as defined above, and an amine of general formula (V)

HR$^6$  (V)

wherein R$^6$ is as defined above, to form the indolinone of the general formula (VI).

The dashed lines in the heterocyclic ring system mean that two double bonds are present but their position is not specified.

A further embodiment the present invention relates to a process for preparing a compound of the general formula (III)

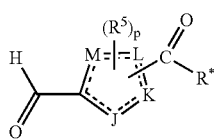

(III)

wherein $R^5$, J, K, L, M, and p are as defined above;

comprising the steps of (i) reacting a compound of general formula (I)

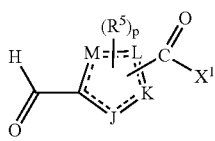
(I)

$R^5$, J, K, L, M, and p are as defined above;
with a compound of general formula (II)

$X^2$—R (II)

(a) wherein one of $X^1$ and $X^2$ is chlorine, or bromine; and the other is selected from the group consisting of hydroxy, —O—$C_{1-4}$ alkyl and —O-phenyl; and R is selected from the group consisting of —(O)—$C_{1-4}$ alkyl, —C(O)—O—($C_{1-4}$)alkyl, —C(O)—O-phenyl, —C(O)—O—$CH_2$-phenyl, wherein the phenyl can optionally be substituted by 1 to 3 halogen atoms;

(b) wherein $X^1$ is chlorine or bromine, $X^2$ is hydrogen and R is selected from the group consisting of

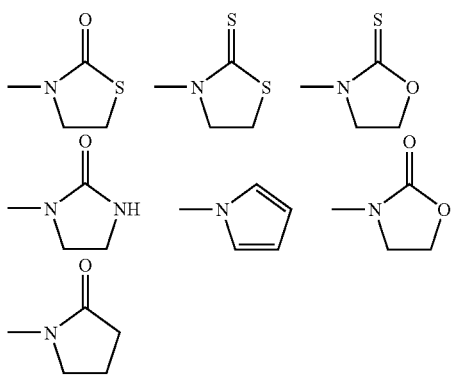

and or (c) wherein $X^1$ is hydroxy, —O—$C_{1-4}$ alkyl and —O-phenyl, and $X^2$ is

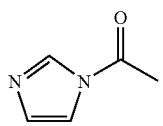

and R is

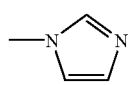

to form a compound of the general formula (III)

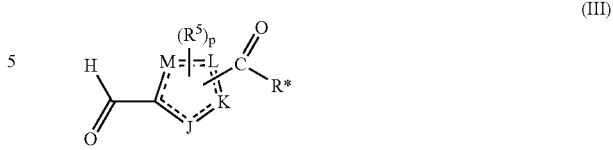
(III)

wherein R* is —O—R in case (a) of step (i) and —R in cases (b) and (c) of step (i).

(ii) reacting the compound of general formula (III) with a compound of general formula (IV)

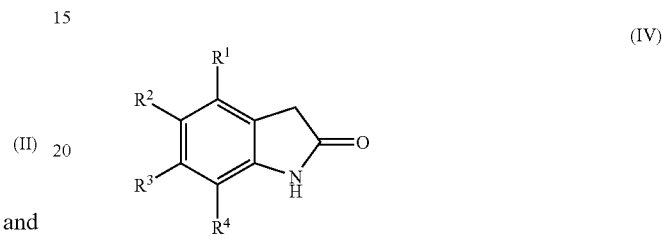
(IV)

wherein $R^1$, $R^2$, $R^3$, and $R^4$ are as defined above,
and an amine of general formula (V)

$HR^6$ (V)

wherein $R^6$ is as defined above, to form the indolinone of the general formula (VI).

The present invention also refers to a process for preparing an indolinone of the general formula (VI)

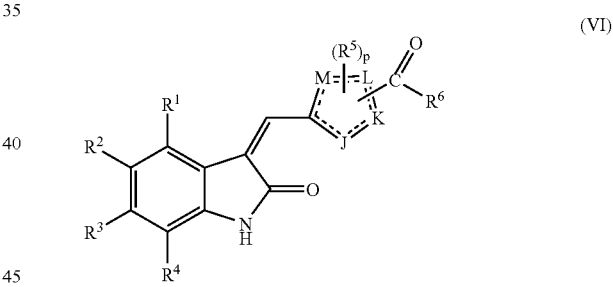
(VI)

wherein
$R^1, R^2, R^3, R^4, R^5, R^6$, J, K, L, M, and p are as defined above;
comprising the steps of
reacting a compound of the general formula (III)

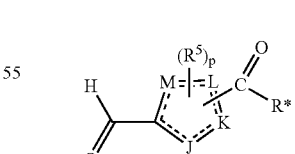
(III)

$R^5$, J, K, L, M, and p are as defined above;
wherein R* is selected from the group consisting of —O—C(O)—$C_{1-4}$ alkyl, —O—C(O)—O—($C_{1-4}$)alkyl, —O—C(O)—O-phenyl, provided that the phenyl may optionally be substituted by 1 to 3 halogen atoms, —O—C(O)—O—$CH_2$-phenyl, provided that the phenyl may optionally be substituted by 1 to 3 halogen atoms,

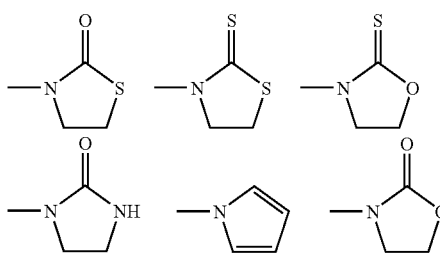

with a compound of general formula (IV)

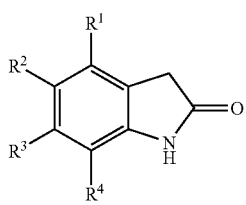

(IV)

$R^1$, $R^2$, $R^3$, and $R^4$ are as defined above;
and an amine of general formula (V)

$$HR^6 \qquad (V)$$

wherein $R^6$ is as defined above, to form the indolinone of the general formula (VI).

In yet another embodiment compounds of the general formula (III):

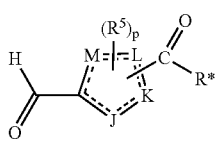

(III)

wherein $R^5$, J, K, L, M, and p are as defined above and R* is selected from the group consisting of —O—C(O)—$C_{1-4}$ alkyl, —O—C(O)—O—($C_{1-4}$)alkyl, —O—C(O)—O-phenyl, provided that the phenyl may optionally be substituted by 1 to 3 halogen atoms, —O—C(O)—O—$CH_2$-phenyl, provided that the phenyl may optionally be substituted by 1 to 3 halogen atoms,

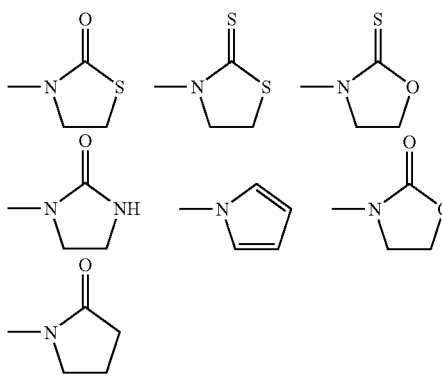

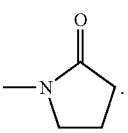

are disclosed. Preferably R* is

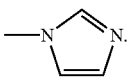

DETAILED DESCRIPTION OF THE INVENTION

The present invention provides a process for preparing indolinone derivatives of general formula (VI). The compounds can modulate the activity of protein kinases and the compounds themselves, their pharmaceutically acceptable salts and derivatives are useful in a wide range of medical applications. Preferred compounds having the formula (VI), pharmaceutical compositions containing such compounds and the medical utility of these compounds have been described, e.g. in WO 01/45689, WO 01/60814, WO 99/48868, U.S. Pat. No. 6,316,429, U.S. Nos. 6,316,635, 6,133,305, and U.S. Pat. No. 6,248,771, all of which are incorporated herein by reference in the entirety. Particularly preferred compounds are described in WO 01/45689 (e.g. compounds 15 and 16) and WO 01/60814 (e.g. in the examples and in Table 1).

The indolinone compounds have the general formula (VI)

(VI)

$R^1$, $R^2$, $R^3$, $R^4$ are independently selected from the group consisting of hydrogen, $C_{1-12}$ alkyl, $C_{1-12}$ alkoxy, $C_{5-12}$ cycloalkyl, $C_{6-12}$ aryl, $C_{5-12}$ heterocyclic group containing 1 to 3 atoms selected from N, S or O, provided that the heterocyclic group may be partially unsaturated, but not aromatic, $C_{6-12}$ aryloxy, $C_{6-12}$ alkaryl, $C_{6-12}$ alkaryloxy, halogen, trihalomethyl, hydroxy, —S(O)R', —$SO_2$NR'R", —$SO_3$R', —SR', —$NO_2$, —NR'R", —OH, —CN, —C(O)R', —OC(O)R', —NHC(O)R', $(CH_2)_nCO_2R'$, and —CONR'R". Preferably $R^1$ is hydrogen or $C_{1-4}$ alkyl; more preferably $R^1$ is hydrogen. In a preferred embodiment $R^2$ is selected from the group consisting of hydrogen, fluorine, chlorine, bromine, $C_{1-4}$ alkyl, —O—$C_{1-4}$ alkyl, phenyl, —COOH, —CN, —C(O)$CH_3$, —$SO_2NH_2$ and —$SO_2N(CH_3)_2$; more preferably $R^2$ is selected from the group consisting of hydrogen, fluorine, chlorine, $C_{1-4}$ alkyl, —O—$C_{1-4}$ alkyl, —CN, —$SO_2NH_2$ and —$SO_2N(CH_3)_2$ and even more preferably $R^2$ is hydrogen, fluorine, chlorine, and $C_{1-4}$ alkyl. Most preferably $R^2$ is fluorine.

In a preferred embodiment $R^3$ is selected from the group consisting of hydrogen, $C_{1-4}$ alkyl, phenyl, $C_{1-4}$ alkoxy and —COOH; more preferably $R^3$ is hydrogen or $C_{1-4}$ alkyl most preferably $R^3$ is hydrogen.

It is preferred that $R^4$ is hydrogen.

Each $R^5$ is independently selected from the group consisting of hydrogen, $C_{1-12}$ alkyl, $C_{1-12}$ alkoxy, $C_{5-12}$ cycloalkyl, $C_{6-12}$ aryl, $C_{5-12}$ heterocyclic group containing 1 to 3 atoms selected from N, S or O, provided that the heterocyclic group may be partially unsaturated, but not aromatic, $C_{6-12}$ aryloxy, $C_{6-12}$ alkaryl, $C_{6-12}$ alkaryloxy, halogen, trihalomethyl, hydroxy, —S(O)R', —SO$_2$NR'R", —SO$_3$R', —SR', —NO$_2$, —NR'R", —OH, —CN, —C(O)R', —OC(O)R', —NHC(O)R', —(CH$_2$)$_n$CO$_2$R', and —CONR'R". Preferably $R^5$ is hydrogen or a $C_{1-4}$ alkyl.

$R^6$ is is selected from —NR$^8$(CH$_2$)$_m$R$^9$ and —NR$^{10}$R$^{11}$, provided that optionally one to two of the CH$_2$ groups may be substituted by —OH or halogen. Preferably $R^6$ is —NR$^8$(CH$_2$)$_m$R$^9$. In a preferred embodiment the CH$_2$ groups are unsubstituted or one of the CH$_2$ groups is substituted by —OH.

$R^8$ is hydrogen or $C_{1-12}$ alkyl. Preferably $R^8$ is hydrogen or $C_{1-4}$ alkyl, and more preferably $R^8$ is hydrogen.

$R^9$ is selected from the group consisting of —NR$^{10}$R$^{11}$, —OH, C(O)R$^{12}$, $C_{6-12}$ aryl, $C_{5-12}$ heterocyclic group containing 1 to 3 atoms selected from N, S or O, —N$^+$(O$^-$)R$^{10}$, and —NHC(O)R$^{13}$. In one embodiment $R^9$ is preferably —NR$^{10}$R$^{11}$. In a second embodiment $R^9$ is preferably a $C_{5-12}$ heterocyclic group containing 1 to 3 atoms selected from N, S or O. Preferably the heterocyclic group is a five- to seven-membered heterocyclic group bonded to the (CH$_2$)$_m$ group via a nitrogen atom and optionally containing a further heteroatom selected from N, O, and S. Examples of the heterocyclic group are, but are not limited to

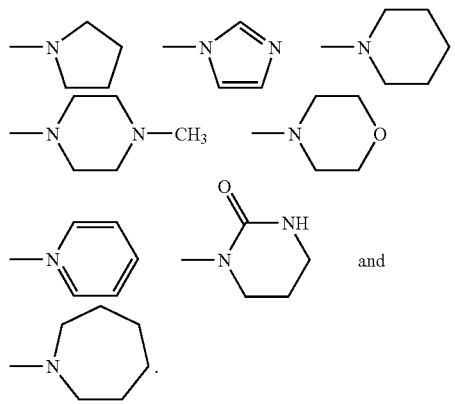

Preferably the heterocyclic group is

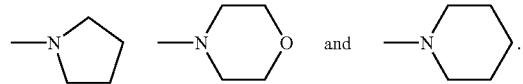

$R^{10}$ and $R^{11}$ are independently selected from the group consisting of hydrogen, $C_{1-12}$ alkyl, $C_{1-12}$ cyanoalkyl, $C_{5-12}$ cycloalkyl, $C_{6-12}$ aryl, and $C_{5-12}$ heterocyclic group containing 1 to 3 atoms selected from N, S or O; or $R^{10}$ and $R^{11}$ may be combined to form a five- or six-membered heterocyclic group optionally containing 1 to 3 atoms selected from N, O, or S in addition to the nitrogen atom to which $R^{10}$ and $R^{11}$ are bound, provided that the heterocyclic group formed by $R^{10}$ and $R^{11}$ may optionally be substituted by R'. Preferably $R^{10}$ and $R^{11}$ are hydrogen or $C_{1-4}$ alkyl. More preferably $R^{10}$ and $R^{11}$ are H.

$R^{12}$ is selected from the group consisting of hydrogen, —OH, $C_{1-12}$ alkoxy and $C_{6-12}$ aryloxy. Preferably $R^{12}$ is a $C_{1-4}$ alkyl.

$R^{13}$ is selected from the group consisting of $C_{1-12}$ alkyl, $C_{1-12}$ haloalkyl, and $C_{6-12}$ aralkyl. Preferably $R^{13}$ is a $C_{1-4}$ alkyl.

R' and R" are independently selected from the group consisting of hydrogen, $C_{1-12}$ alkyl, $C_{1-12}$ cyanoalkyl, $C_{5-12}$ cycloalkyl, $C_{6-12}$ aryl, $C_{5-12}$ heterocyclic group containing 1 to 3 atoms selected from N, S or O, provided that the heterocyclic group may be partially unsaturated, but not aromatic, or in the group —NR'R" the R' and R" substituents may be combined to form a five- or six-membered heterocyclic group optionally containing 1 to 3 atoms selected from N, O, or S in addition to the nitrogen atom to which R' and R" are bound. Preferably R' and R" are independently a $C_{1-4}$ alkyl.

J is selected from the group consisting of O, S, and NH, preferably J is NH one of K, L and M is C and the group —C(O)R$^6$ is bound thereto, the others of the group of K, L and M are independently selected from the group consisting of CR$^5$, CR$^5_2$, N, NR$^5$, O and S. Preferred heterocyclic groups

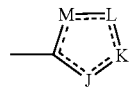

are

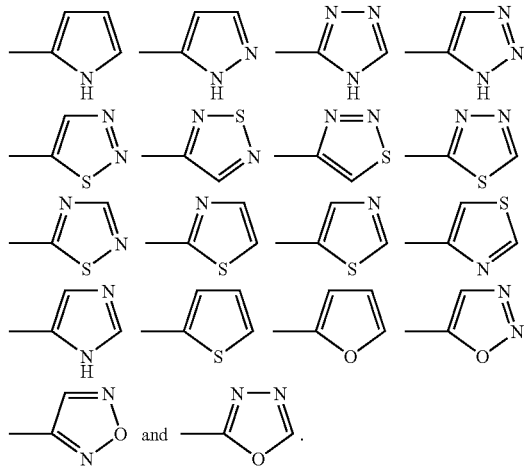

Particularly preferred as the heterocyclic group is

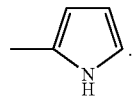

n is 0, 1 or 2.

m is 1, 2, 3, or 4; preferably m is 2 or 3.

p is 0, 1 or 2.

Preferred compounds are shown wherein X is a halogen

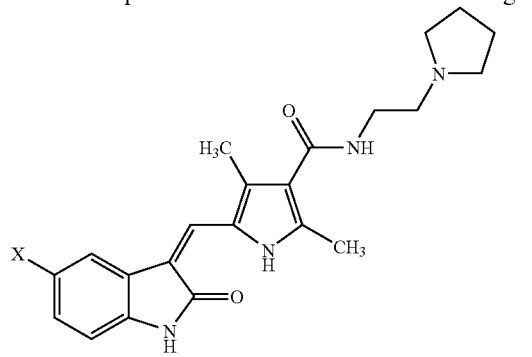

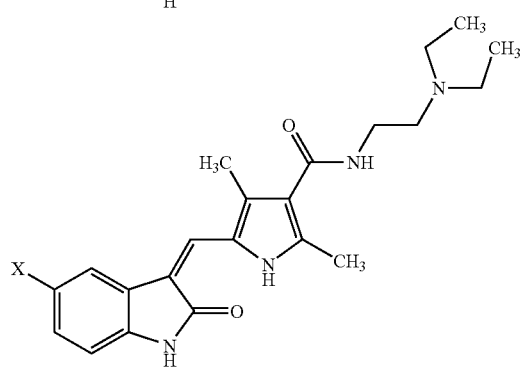

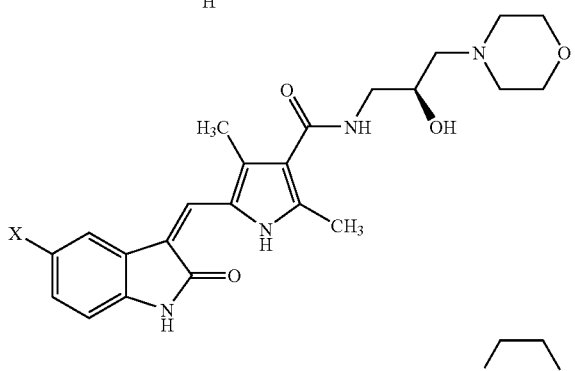

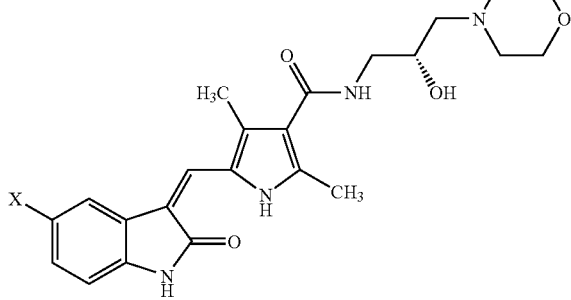

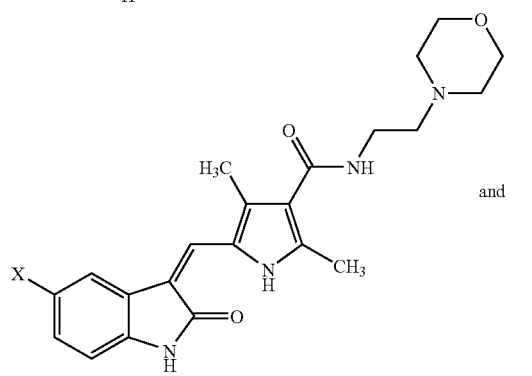

and

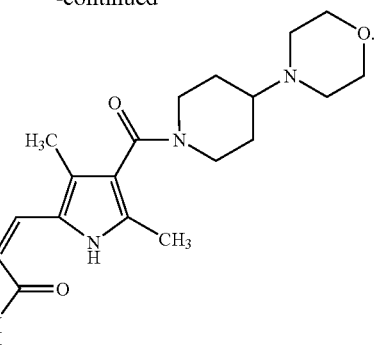

In the first step of the process of the present invention, a compound of general formula (I)

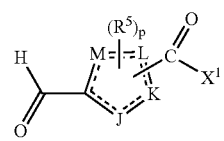
(I)

wherein $R^5$, $R^6$, J, K, L, M and p are as defined above, is reacted with a compound of general formula (II)

$$X^2\text{—}R \tag{II}$$

(a) wherein one of $X^1$ and $X^2$ is chlorine, or bromine; and the other is selected from the group consisting of hydroxy, —O—$C_{1-4}$ alkyl and —O-phenyl; and R is selected from the group consisting of —C(O)—$C_{1-4}$ alkyl, —C(O)—O—($C_{1-4}$)alkyl, —C(O)—O-phenyl, provided that the phenyl may optionally be substituted by 1 to 3 halogen atoms, —(O)—O—$CH_2$-phenyl, provided that the phenyl may optionally be substituted by 1 to 3 halogen atoms, (b) wherein $X^1$ is chlorine or bromine, $X^2$ is hydrogen and R is selected from the group consisting of

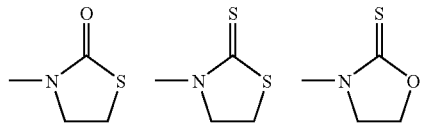

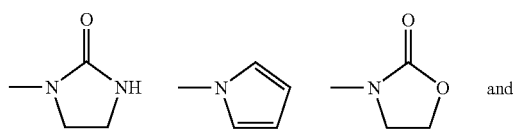 and

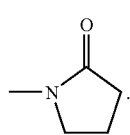

or (c) wherein $X^1$ is hydroxy, —O—$C_{1-4}$ alkyl and O-phenyl, and $X^2$ is

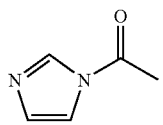

and R is

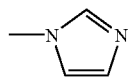

to form a compound of the general formula (III)

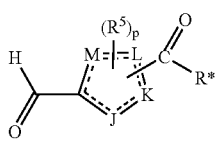
(III)

wherein R* is —O—R in case (a) of step (1) and —R in cases (b) and (c) of first step. In first step, option (c) is preferred.

The compounds of general formulae (I) and (II) are either commercially available or can be prepared by methods well known in the art. For example, heterocycles having a formyl group can be obtained by slowly adding $POCl_3$ to dimethylformamide followed by addition of the appropriate heterocycle, which is also dissolved in dimethylformamide. This reaction is described in more detail and exemplified e.g. in WO 01/60814, which is incorporated herein by reference.

The reaction is generally carried out in a polar aprotic solvent. An aprotic solvent is any solvent that, under normal reaction conditions, does not donate a proton to a solute. Polar solvents are those which have a non-uniform distribution of charge. Generally they include 1 to 3 atoms selected from heteroatom such as N, S or O. Examples of polar aprotic solvents that can be used in the invention are ethers such as tetrahydrofuran, diethylether, methyl tert-butyl ether, nitrile solvents such as acetonitrile, and amide solvents such as dimethylformamide. Preferably the reaction solvent is an ether, more preferably the solvent is tetrahydrofuran. Mixtures of the solvents may also be employed. The aprotic, polar solvent preferably has a boiling point from 30° C. to 130° C., more preferably from 50° C. to 80° C. Both components of the reaction are introduced into a reaction vessel together with the solvent. The reactants may be added in any order, although it is preferred to add compound I to a stirred suspension of compound II in a suitable solvent, at room temperature (18–25° C.). A reactant concentration of 0.3 to 0.5 moles/liter is preferred, although the person of skill in the art will appreciate that the reaction may be conducted at different concentrations. The reaction may be conducted at a temperature of 0° C. up to the reflux temperature of the solvent. However, it is preferred to conduct the reaction at a temperature of 25° C. to 80° C. with mechanical stirring. The progress of the reaction may be monitored by a suitable analytical method, such as HPLC. Upon completion of the reaction the reaction mixture is cooled and the intermediate compound III crystallizes. It is preferred to cool the reaction mixture to a temperature below room temperature and 0° C. is most preferred. The intermediate compound III may be separated from the reaction mixture by methods known to those skilled in the art, such as centrifuging, and filtration. Intermediate III is a crystalline solid that is non-hygroscopic and is stable in air at room temperature.

The compound of general formula (III) is then reacted in a second step with a compound of general formula (IV)

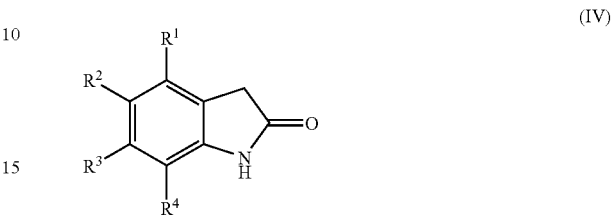
(IV)

wherein $R^1$, $R^2$, $R^3$ $R^4$ are as defined above and an amine of general formula (V)

$HR^6$ (V)

wherein $R^6$ is as defined above to form the indolinone of the general formula (VI). The reaction can be carried out in solution, using the same solvents used in the first reaction step. The reaction may be carried out sequentially by reacting compound III with either compound compound IV or compound V and then adding the other compound. However, it is preferred that compounds II, IV and V are introduced into a reaction vessel together with the solvent. The reactants may be added in any order, although it is preferred to add compound III to a stirred suspension of compound IV and the amine V in a suitable solvent, at room temperature (18–25° C.). A reactant concentration of 0.3 to 0.5 moles/liter is preferred, although the person of skill in the art will appreciate that the reaction may be conducted at different concentrations. The reaction may be conducted at a temperature of 50° C. up to the reflux temperature of the solvent. However, it is preferred to conduct the reaction at a temperature of 50° C. to 80° C. with mechanical stirring. The progress of the reaction may be monitored by a suitable analytical method, such as HPLC. Upon completion of the reaction, the reaction mixture is cooled and compound VI crystallizes. It is preferred to cool the reaction mixture to a temperature below room temperature and 0° C. is most preferred. Compound VI may be separated from the reaction mixture by methods known to those skilled in the art, such as centrifuging, and filtration. Although Compound VI obtained from the process above is often of sufficient purity for medical use, if desired, compound VI may be further purified by methods known to those skilled in the art, such as recrystallization.

If desired the indolinone compounds of general formula (VI) can be further reacted to their pharmaceutically acceptable salts or derivatives according to conventional processes.

The present invention provides a process for preparing indolinone derivatives, which is more convenient than the prior art processes. Generally the intermediates are easier to handle. Furthermore, product isolation is facilitated.

The following examples serve to illustrate the invention and should not be construed as limiting. Unless otherwise specified all percentages, parts, and amounts are based on weight.

EXAMPLES

Example 1

N-[2-(diethylamino)ethyl]-5-[(Z)-(5-fluoro-2-oxo-1,2-dihydro-3H-indol-3-ylidene)methyl]-2,4-dimethyl-1H-pyrrole-3-carboxamide

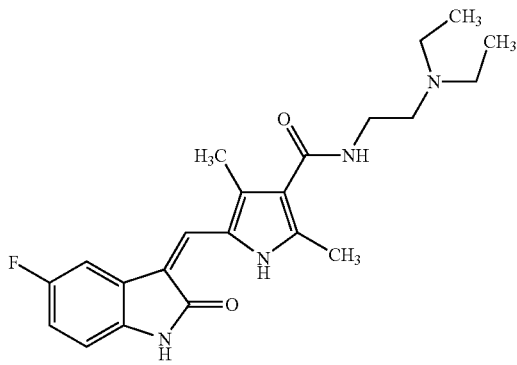

4-(1H-imidazol-1-ylcarbonyl)-3,5-dimethyl-1H-pyrrole-2-carbaldehyde (14.0 g), N,N-diethylethylenediamine (15.0 g), 5-fluorooxindole (9.86 g), triethylamine (27 ml), and acetonitrile (250 ml) were mixed and heated to 60° C. The black slurry was stirred for 18 h at 60° C. (needs mechanical stirrer). The resulting yellow slurry was cooled to room temperature, diluted with 100 ml acetonitrile, and filtered. The cake was washed with 3×100 ml acetonitrile and dried overnight at 50° C. under house vacuum. N-[2-(diethylamino)ethyl]-5-[(Z)-(5-fluoro-2-oxo-1,2-dihydro-3H-indol-3-ylidene)methyl]-2,4-dimethyl-1H-pyrrole-3-carboxamide (21.7 g) was obtained with 85% yield.

Example 2

5-[(Z)-(5-bromo-2-oxo-1,2-dihydro-3H-indol-3-ylidene)methyl]-N-[2-(diethylamino)ethyl]-2,4-dimethyl-1H-pyrrole-3-carboxamide

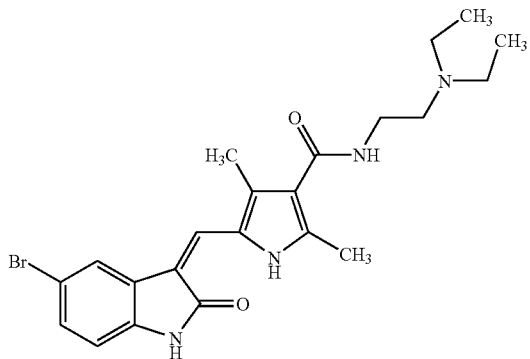

A 0.1 L flask fitted with a thermometer, condenser, beating mantle, nitrogen inlet and magnetic stirring was charged with, 3.0 g 5-Bromooxindole, 3.03 g 4-(1H-imidazol-1-ylcarbonyl)-3,5-dimethyl-1H-pyrrole-2-carbaldehyde, 3.24 g N,N-Diethylethylene diamine, 4.23 g Triethylamine and 30 ml Tetrahydrofuran. The mixture was heated to 60–65° C. for 8 hours, then cooled to ambient temperature. 10 ml Tetrahydrofuran was added to aid stirring and the reaction mixture was filtered. Drying provided 3.7 g (57.7%) first crop of 5-[(Z)-(5-bromo-2-oxo-1,2-dihydro-3H-indol-3-ylidene)methyl]-N-[2-(diethylamino)ethyl]-2,4-dimethyl-1H-pyrrole-3-carboxamide. The mother liquors are cooled to −10° C. for 6 h for an additional 1.9 g (29.6%). 1HNMR (DMSO): δ 8.08 (1H, s); 7.75 (1H, s); 7.41 (1H, s); 7.24 (1H, d); 6.81 (1H, d); 3.31 (4H, bs); 2.46 (14H, bm); 0.96 (6H, t).

Example 3

5-[(Z)-(5-fluoro-2-oxo-1,2-dihydro-3H-indol-3-ylidene)methyl]-N-[(2R)-2-hydroxy-3-morpholin-4-ylpropyl]-2,4-dimethyl-1H-pyrrole-3-carboxamide

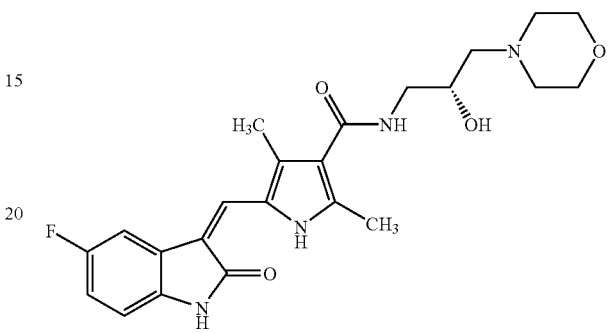

A 0.25 L flask fitted with a thermometer, condenser, magnetic stirring, and nitrogen inlet was charged with 4.92 g 5-Fluorooxindole, 7.0 g 4-(1H-imidazol-1-ylcarbonyl)-3,5-dimethyl-1H-pyrrole-2-carbaldehyde, 15.5 g (R)-1-Amino-3-(4-morpholinyl)-2-propanol, 9.78 g Triethylamine and 88 ml Tetrahydrofuran. The mixture was heated to 60° C. for 16.5 hours. The reaction was cooled to ambient temperature and filtered. The solids obtained were slurried (3) three successive times in acetonitrile at 11 ml/g, dried in vacuoto produce a yield of 3.6 g (25.25%) of 5-[(Z)-(5-fluoro-2-oxo-1,2-dihydro-3H-indol-3-ylidene)methyl]-N-[(2R)-2-hydroxy-3-morpholin-4-ylpropyl]-2,4-dimethyl-1H-pyrrole-3-carboxamide.

1HNMR (DMSO): δ 10.86 (1H, bs); 7.75 (1H, d); 7.70 (1H, s); 7.50 (1H, m), 6.88 (2H, m), 4.72 (1H, bs); 3.78 (1H, bs); 3.56 (4H, m); 3.32 (6H, m); 3.15 (1H, m), 2.43 (8H, bm).

Example 4

5-[(Z)-(5-chloro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide

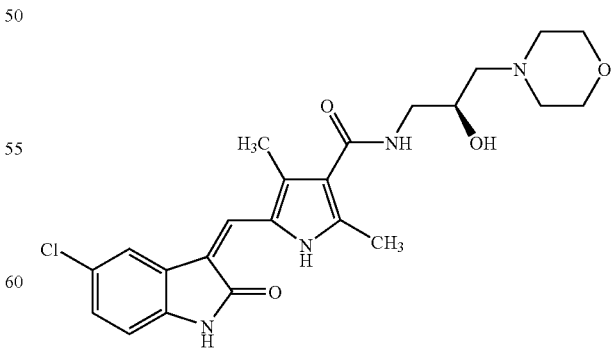

4-(1H-imidazol-1-ylcarbonyl)-3,5-dimethyl-1H-pyrrole-2-carbaldehyde (6.8 g, 31.3 mmol), (2S)-1-amino-3-morpholin-4-ylpropan-2-ol (10.0 g, 62.5 mmol), 5-chlorooxindole (5.3 g, 31.6 mmol), and THF (100 ml) were mixed and heated to 60° C. After stirring for 68 h at 60° C., triethylamine (14 ml) was added and stirred for 5 h at 60° C. Added 4.6 g of (2S)-1-amino-3-morpholin-4-ylpropan-2-ol, and stirred for 20 h at 60° C. The yellow slurry was cooled to room temperature and filtered. The cake was washed with 2×50 ml THF and dried overnight at 50° C. under house vacuum. 5-[(Z)-(5-chloro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide (5.48 g) was obtained with 38% yield.

Example 5

5-[(Z)-(5-fluoro-2-oxo-1,2-dihydro-3H-indol-3-ylidene)methyl]-2,4-dimethyl-N-(2-pyrrolidin-1-ylethyl)-1H-pyrrole-3-carboxamide

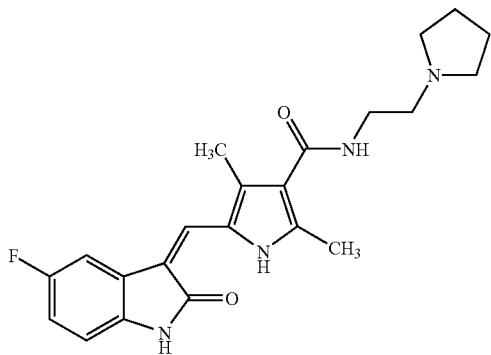

A mixture of 4-(1H-imidazol-1-ylcarbonyl)-3,5-dimethyl-1H-pyrrole-2-carbaldehyde (4.1 Kg), THF (70.8 Kg), and water (4.7 L) were heated at 40–50° C. until the solids were dissolved. The resulting solution was filtered, and then distilled to 40–50. The mixture was subsequently cooled to 25–30° C. A solution of 1-(2-aminoethyl) pyrrolidine (2.8 Kg) in THF (2.1 L) was added. A solution of 5-Fluorooxindole (2.9 Kg) in THF (18.8 Kg) was also added. The mixture was then heated to 45–50° C. for 17 h. The mixture was cooled, filtered, washed with THF (28 Kg), and dried at 45–50° C. to afford 5.53 Kg (73%) of 5-[(Z)-(5-fluoro-2-oxo-1,2-dihydro-3H-indol-3-ylidene)methyl]-2,4-dimethyl-N-(2-pyrrolidin-1-ylethyl)-1H-pyrrole-3-carboxamide.

1H NMR (DMSO-d6) δ 2.48 (d, J=8 Hz, 6H), 2.55 (m, 7H), 2.62 (t, J=8 Hz, 1H), 3.37 (m, 6H), 6.90 (m, 1H), 7.00 (m, 1H), 7.57 (t, J=4 Hz, 1H), 7.80 (m, 2H).

Example 6

5-[(Z)-(5-chloro-2-oxo-1,2-dihydro-3H-indol-3-ylidene)methyl]-N-[(2R)-2-hydroxy-3-morpholin-4-ylpropyl]-2,4-dimethyl-1H-pyrrole-3-carboxamide

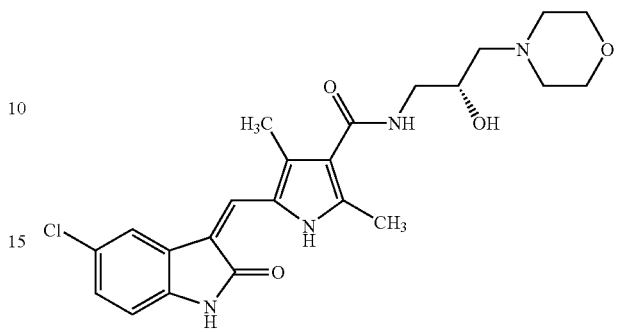

4-(1H-imidazol-1-ylcarbonyl)-3,5-dimethyl-1H-pyrrole-2-carbaldehyde (7.0 g, 32.3 mmol), (2R)-1-amino-3-morpholin-4-ylpropan-2-ol (15.5 g, 96.9 mmol), 5-chlorooxindole (5.48 g, 32.6 mmol), triethylamine (14 ml), and THF (88 ml) were mixed and heated to 60° C. A red solution formed. After stirring for 16 h at 60° C., the yellow slurry was cooled to room temperature and filtered. The cake was washed with 2×50 ml of THF and dried overnight at 50° C. under house vacuum. 5-[(Z)-(5-chloro-2-oxo-1,2-dihydro-3H-indol-3-ylidene)methyl]-N-[(2R)-2-hydroxy-3-morpholin-4-ylpropyl]-2,4-dimethyl-1H-pyrrole-3-carboxamide (4.36 g) was obtained in 29% yield.

Example 7

5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide

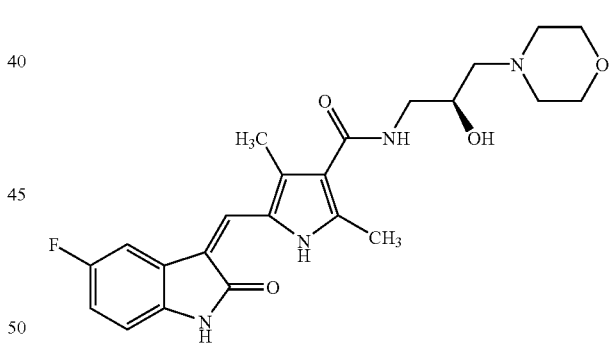

4-(1H-imidazol-1-ylcarbonyl)-3,5-dimethyl-1H-pyrrole-2-carbaldehyde (7.0 g, 32.3 mmol), (2S)-1-amino-3-morpholin-4-ylpropan-2-ol (15.0 g, 64.6 mmol), 5-fluorooxindole (4.93 g, 32.6 mmol), triethylamine (9.79 g, 96.9 mmol), and THF (88 ml) were mixed and heated to 60° C. After stirring for 24 h at 60° C., the mixture was cooled to rt and filtered. The cake was washed with 80 ml THF and dried overnight at 50° C. under house vacuum. A brown solid (23.2 g) was obtained. The solid was slurried in 350 ml water for 5 h at room temperature and filtered. The cake was washed with 100 ml water and dried at 50° C. under house vacuum overnight. 5-[(Z)-(5-fluoro-2-oxo-1,2-dihydro-3H-indol-3-ylidene)methyl]-N-[(2S)-2-hydroxy-3-morpholin-4-ylpropyl]-2,4-dimethyl-1H-pyrrole-3-carboxamide (8.31 g) was obtained in 56% yield.

Example 8

5-[(Z)-(5-fluoro-2-oxo-1,2-dihydro-3H-indol-3-ylidene)methyl]-2,4-dimethyl-N-(2-morpholin-4-ylethyl)-1H-pyrrole-3-carboxamide

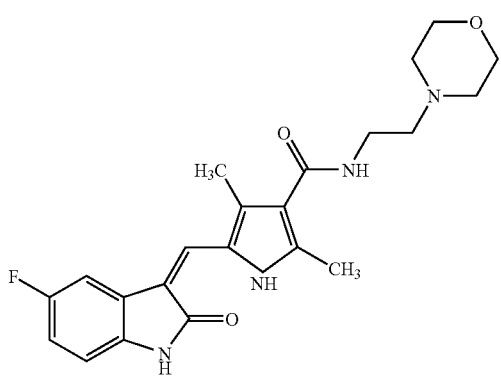

4-(1H-imidazol-1-ylcarbonyl)-3,5-dimethyl-1H-pyrrole-2-carbaldehyde (5.0 g, 23.0 mmol), 4-(2-aminoethyl)morpholine (4.5 g, 34.6 mmol), 5-fluorooxindole (3.47 g, 23.0 mmol), and THF (80 ml) were mixed and heated to 65° C. After stirring for 24 h at 65° C., the mixture was cooled to room temperature and filtered. The cake was washed with 40 ml THF and dried overnight at 50° C. under house vacuum. 5-[(Z)-(5-fluoro-2-oxo-1,2-dihydro-3H-indol-3-ylidene)methyl]-2,4-dimethyl-N-(2-morpholin-4-ylethyl)-1H-pyrrole-3-carboxamide (8.28 g) was obtained in 87% yield.

Example 9

(3Z)-3-({3,5-dimethyl-4-[(4-morpholin-4-ylpiperidin-1-yl)carbonyl]-1H-pyrrol-2-yl}methylene)-5-fluoro-1,3-dihydro-2H-indol-2-one

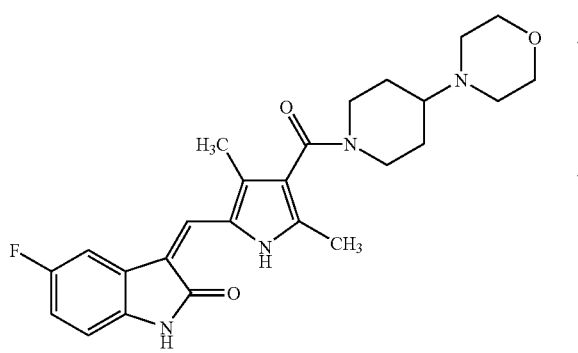

4-(1H-imidazol-1-ylcarbonyl)-3,5-dimethyl-1H-pyrrole-2-carbaldehyde (11.3 g, 51.9 mmol), 4-morpholinopiperidine (15.0 g, 88.2 mmol), 5-fluorooxindole (7.84 g, 51.9 mmol), and THF (126 ml) were mixed and heated to 66° C. After stirring for 68 h at 66° C., the mixture was cooled to room temperature and filtered. The cake was washed with 4×20 ml THF and dried overnight at 70° C. under house vacuum. (3Z)-3-({3,5-dimethyl-4-[(4-morpholin-4-ylpiperidin-1-yl)carbonyl]-1H-pyrrol-2-yl}methylene)-5-fluoro-1,3-dihydro-2H-indol-2-one 16.09 g was obtained in 68% yield.

What is claimed is:

1. A process for preparing an indolinone of the general formula (VI)

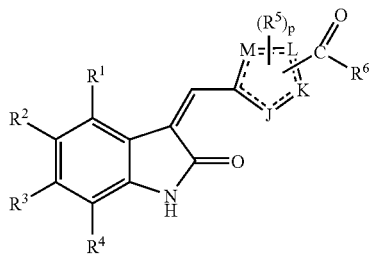

(VI)

wherein $R^1$, $R^2$, $R^3$, $R^4$ are independently selected from the group consisting of hydrogen, $C_{1-12}$ alkyl, $C_{1-12}$ alkoxy, $C_{5-12}$ cycloalkyl, $C_{6-12}$ aryl, $C_{5-12}$ heterocyclic group containing 1 to 3 atoms selected from N, S or O, provided that the heterocyclic group may be partially unsaturated, but not aromatic, $C_{6-12}$ aryloxy, $C_{6-12}$ alkaryl, $C_{6-12}$ alkaryloxy, halogen, trihalomethyl, hydroxy, —S(O)R', —SO$_2$NR'R", —SO$_3$R', —SR', —NO$_2$, —NR'R", —OH, —CN, —C(O)R', —OC(O)R', —NHC(O)R', —(CH$_2$)$_n$CO$_2$R', and —CONR'R";

each $R^5$ is independently selected from the group consisting of hydrogen, $C_{1-12}$ alkyl, $C_{1-12}$ alkoxy, $C_{5-12}$ cycloalkyl, $C_{6-12}$ aryl, $C_{5-12}$ heterocyclic group containing 1 to 3 atoms selected from N, S or O, provided that the heterocyclic group may be partially unsaturated, but not aromatic, $C_{6-12}$ aryloxy, $C_{6-12}$ alkaryl, $C_{6-12}$ alkaryloxy, halogen, trihalomethyl, hydroxy, —S(O)R', —SO$_2$NR'R", —SO$_3$R', —SR', —NO$_2$, —NR'R", —OH, —CN, —C(O)R', —OC(O)R', —NHC(O)R', —(CH$_2$)$_n$CO$_2$R', and —CONR'R";

$R^6$ is is selected from —NR$^8$(CH$_2$)$_m$R$^9$ and —NR$^{10}$R$^{11}$, provided that optionally one to two of the CH$_2$ groups may be substituted by —OH or halogen;

$R^8$ is hydrogen or $C_{1-12}$ alkyl;

$R^9$ is selected from the group consisting of —NR$^{10}$R$^{11}$, —OH, —C(O)R$^{12}$, $C_{6-12}$ aryl, $C_{5-12}$ heterocyclic group containing 1 to 3 atoms selected from N, S or O, —N$^+$(O$^-$)R$^{10}$, and —NHC(O)R$^{13}$;

$R^{10}$ and $R^{11}$ are independently selected from the group consisting of hydrogen, $C_{1-12}$ alkyl, $C_{1-12}$ cyanoalkyl, $C_{5-12}$ cycloalkyl, $C_{6-12}$ aryl, and $C_{5-12}$ heterocyclic group containing 1 to 3 atoms selected from N, S or O; or $R^{10}$ and $R^{11}$ may be combined to form a five- or six-membered heterocyclic group optionally containing 1 to 3 atoms selected from N, O, or S in addition to the nitrogen atom to which $R^{10}$ and $R^{11}$ are bound, provided that the heterocyclic group formed by $R^{10}$ and $R^{11}$ may optionally be substituted by R'

$R^{12}$ is selected from the group consisting of hydrogen, —OH, $C_{1-12}$ alkoxy and $C_{6-12}$ aryloxy;

$R^{13}$ is selected from the group consisting of $C_{1-12}$ alkyl, $C_{1-12}$ haloalkyl, and $C_{6-12}$ aralkyl;

R' and R" are independently selected from the group consisting of hydrogen, $C_{1-12}$ alkyl, $C_{1-12}$ cyanoalkyl, $C_{5-12}$ cycloalkyl, $C_{6-12}$ aryl, $C_{5-12}$ heterocyclic group containing 1 to 3 atoms selected from N, S or O, provided that the heterocyclic group may be partially unsaturated, but not aromatic, or in the group —NR'R", R' and R" may be combined to form a five- or six-membered heterocyclic group optionally containing 1 to 3 atoms selected from N, O, or S in addition to the nitrogen atom to which R' and R" are bound;

Halo is a substituent selected from the group consisting of F, Cl, Br, and I

J is selected from the group consisting of O, S, and NH;

one of K, L and M is C and the group —C(O)R⁶ is bound thereto, the others of the group of K, L and M are independently selected from the group consisting of $CR^5$, $CR^5_2$, N, $NR^5$, O and S;

n is 0, 1 or 2;

m is 1, 2, 3, or 4; and p is 0, 1 or 2;

comprising the steps of (i) reacting a compound of general formula (I)

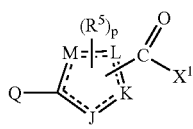

Formula I wherein $R^5$, J, K, L, M and p are as defined above,

Q is selected from the group consisting of

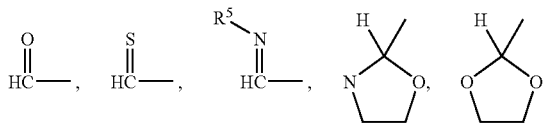

with a compound of general formula (II)

$X^2$—R (II)

wherein:

(a) one of $X^1$ and $X^2$ is chlorine, or bromine, and the other is selected from the group consisting of hydroxy, —O—$C_{1-4}$ alkyl and —O-phenyl, and R is selected from the group consisting of C(O)—$C_{1-4}$ alkyl, —C(O)—O—($C_{1-4}$)alkyl, —C(O)—O-phenyl, provided that the phenyl may optionally be substituted by 1 to 3 halogen atoms, —C(O)—O—CH₂-phenyl, provided that the phenyl may optionally be substituted by 1 to 3 halogen atoms, or (b) $X^1$ is chlorine or bromine, $X^2$ is hydrogen and R is selected from the group consisting of

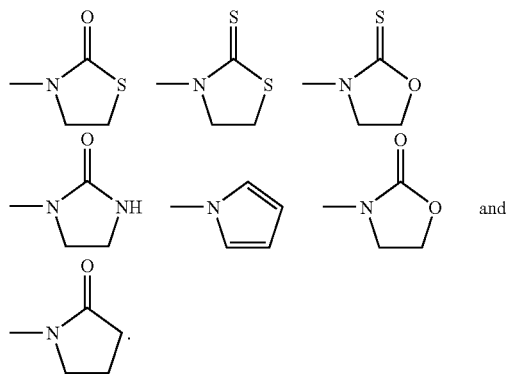

or (c) $X^1$ is hydroxy, —O—$C_{1-4}$ alkyl and —O-phenyl, $X^2$ is

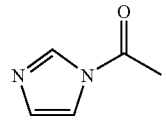

and R is

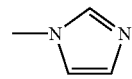

to form a compound of the general formula (III)

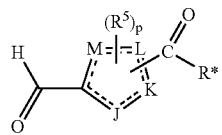

(III)

wherein R* is —O—R in case (a) of step (i) and —R in cases (b) and (c) of step (i);

(ii) reacting the compound of general formula (III) with a compound of general formula (IV)

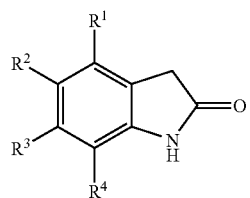

(IV)

wherein $R^1$, $R^2$, $R^3$, and $R^4$ are as defined above, and an amine of general formula (V)

HR⁶ (V)

wherein $R^6$ is as defined above, to form the indolinone of the general formula (VI).

2. The process according to claim 1, wherein

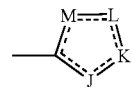

is selected from the group consisting of

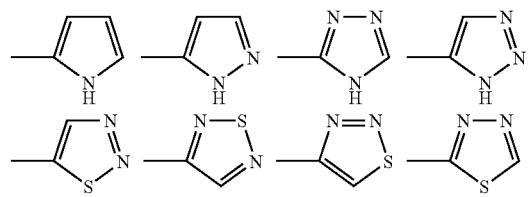

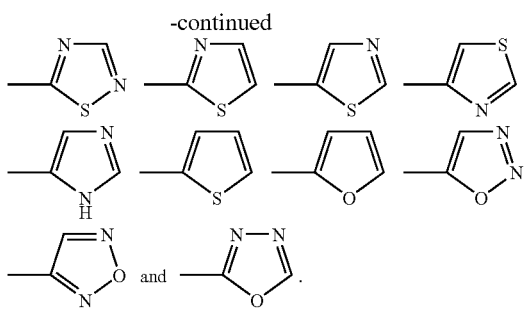

3. The process according to claim 1, wherein $\underset{J}{\overset{M=L}{\underset{K}{\bigtriangleup}}}$ is $\underset{H}{\bigcirc_{N}}$.

4. The process according to claim 1, wherein $R^1$ is hydrogen or $C_{1-4}$ alkyl.

5. The process according to claim 1, wherein $R^1$ is hydrogen.

6. The process according to claim 1, wherein $R^2$ is selected from the group consisting of hydrogen, fluorine, chlorine, bromine, $C_{1-4}$ alkyl, —O—$C_{1-4}$ alkyl, phenyl, —COOH, —CN, —C(O)CH$_3$, —SO$_2$NH$_2$ and —SO$_2$N(CH$_3$)$_2$.

7. The process according to claim 1, wherein $R^2$ is selected from the group consisting of hydrogen, fluorine, chlorine, bromine, $C_{1-4}$ alkyl, —O—$C_{1-4}$ alkyl, —CN, —SO$_2$NH$_2$ and —SO$_2$N(CH$_3$)$_2$.

8. The process according to claim 1, wherein $R^2$ is selected from the group consisting of hydrogen, fluorine, chlorine, and bromine.

9. The process according to claim 1, wherein $R^2$ is fluorine.

10. The process according to claim 1, wherein $R^3$ is selected from the group consisting of hydrogen, $C_{1-4}$ alkyl, phenyl, —O—$C_{1-14}$ alkyl and —COOH.

11. The process according to claim 1, wherein $R^3$ is hydrogen or $C_{1-4}$ alkyl.

12. The process according to claim 1, wherein $R^3$ is hydrogen.

13. The process according to claim 1, wherein $R^4$ is hydrogen.

14. The process according to claim 1, wherein $R^5$ is selected from the group consisting of hydrogen, $C_{1-4}$ alkyl, —C(O)—$C_{1-4}$ alkyl, —C(O)-phenyl, and phenyl.

15. The process according to claim 1, wherein $R^5$ is hydrogen, or $C_{1-4}$ alkyl.

16. The process according to claim 1, wherein $R^6$ is —NR$^8$(CH$_2$)$_m$R$^9$, provided that one or two of the CH$_2$ groups can optionally be substituted by —OH or halogen.

17. The process according to claim 1, wherein $R^8$ is hydrogen or $C_{1-4}$ alkyl.

18. The process according to claim 1, wherein m is 2 or 3.

19. The process according to claim 1, wherein $R^9$ is —NR$^{10}$R$^{11}$.

20. The process according to claim 19, wherein $R^{10}$ and $R^{11}$ are hydrogen or $C_{1-4}$ alkyl.

21. The process according to claim 1, wherein $R^9$ is a $C_{5-12}$ heterocyclic group containing 1 to 3 atoms selected from N, S or O.

22. The process according to claim 21, wherein the heterocyclic group is a five- to seven-membered heterocyclic group bonded to the (CH$_2$)$_m$ group via a nitrogen atom and optionally containing a further heteroatom selected from N, O, and S.

23. The process according to claim 22, wherein the heterocyclic group is selected from the group consisting of 24. The process of claim 23, wherein the heterocyclic group is selected from the group consisting of 25. The process according to claim 16, wherein $R^8$ is hydrogen or $C_{1-4}$ alkyl.

26. The process according to claim 16, wherein m is 2 or 3.

27. The process according to claim 16, wherein $R^9$ is —NR$^{10}$R$^{11}$.

28. The process according to claim 27, wherein $R^{10}$ and $R^{11}$ are hydrogen or $C_{1-4}$ alkyl.

29. The process according to claim 16, wherein $R^9$ is a $C_{5-12}$ heterocyclic group containing 1 to 3 atoms selected from N, S or O.

30. The process according to claim 29, wherein the heterocyclic group is a five- or six-membered heterocyclic group bonded to the (CH$_2$)$_m$ group via a nitrogen atom and optionally containing a further heteroatom selected from N, O, and S.

31. The process according to claim 30, wherein the heterocyclic group is selected from the group consisting of 32. The process of claim 31, wherein the heterocyclic group is selected from the group consisting of

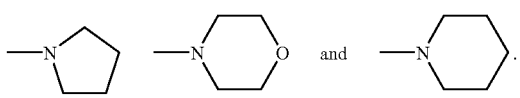

33. The process according to claim 1, wherein the compounds of general formula (I) and general formula (II) are reacted in a polar, aprotic solvent.

34. The process according to claim 33, wherein the polar, aprotic solvent is an ether.

35. The process according to claim 33, wherein the compounds of general formula (I) and general formula (II) are reacted at a temperature in the range of from about 0° C. to about the temperature at which the reaction mixture refluxes.

36. The process according to claim 1, wherein the compounds of general formula (III), general formula (IV) and general formula (V) are reacted in a polar, aprotic solvent.

37. The process according to claim 36, wherein the polar, aprotic solvent is an ether.

38. The process according to claim 36, wherein the compounds of general formula (III), general formula (IV) and general formula (V) are reacted at a temperature in the range of from about +50° C. to about the temperature at which the reaction mixture refluxes.

39. The process according to claim 1, wherein the compounds of general formula (III), general formula (IV) and general formula (V) are reacted in a one-pot reaction.

40. The process according to claim 1, wherein the compound of general formula (VI) is selected from the group consisting of:

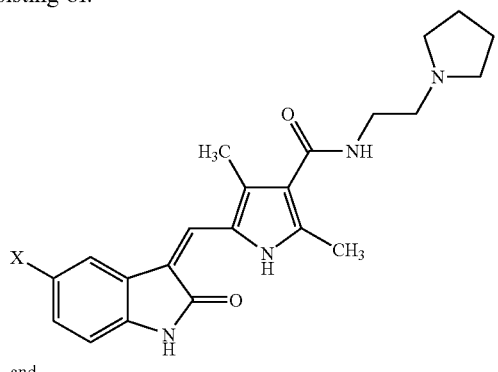

and

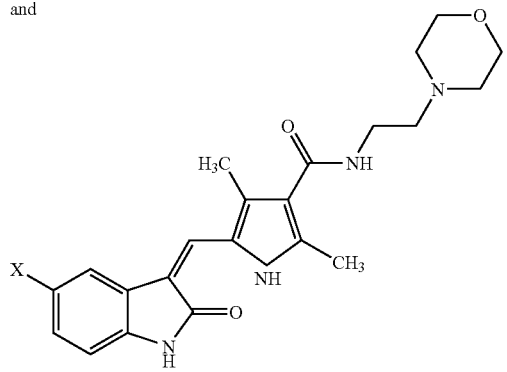

wherein X is selected from the group consisting of hydrogen, fluorine, chlorine and bromine.

41. The process according to claim 40, wherein X is fluorine.

42. The process of claim 1, wherein the compound of the general formula (VI) is further converted into a pharmaceutically acceptable salt or derivative.

43. The process according to claim 1, wherein the compound of general formula (VI) is selected from the group consisting of:

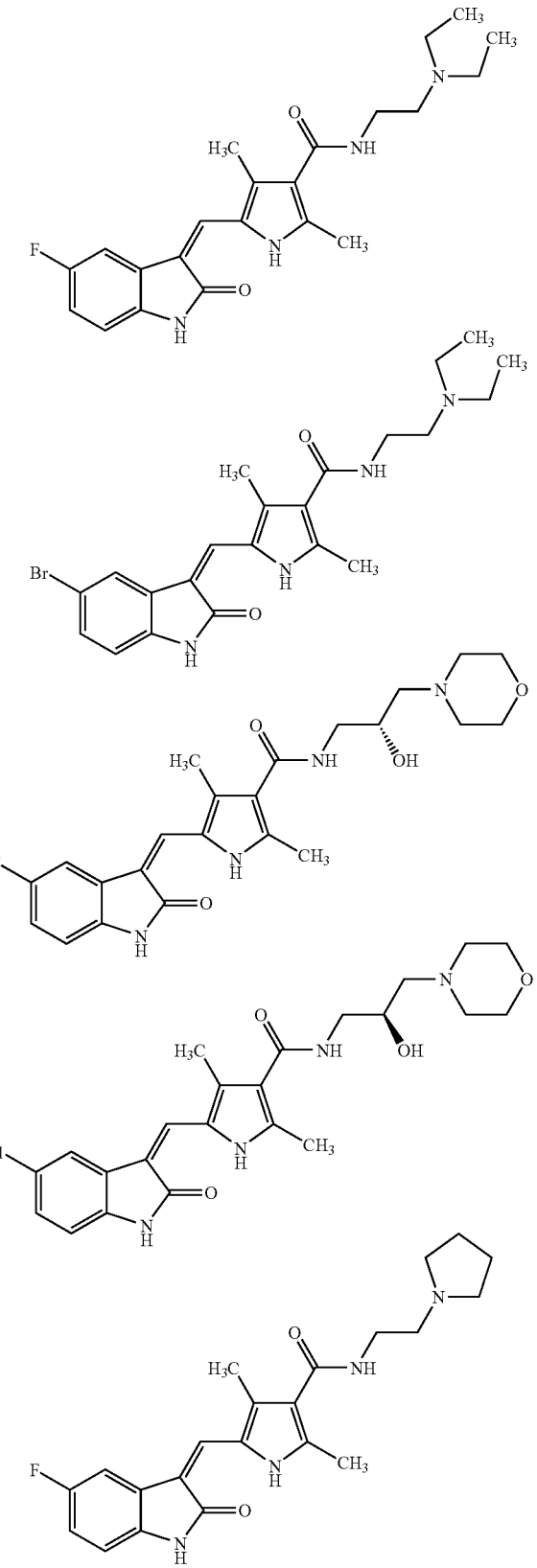

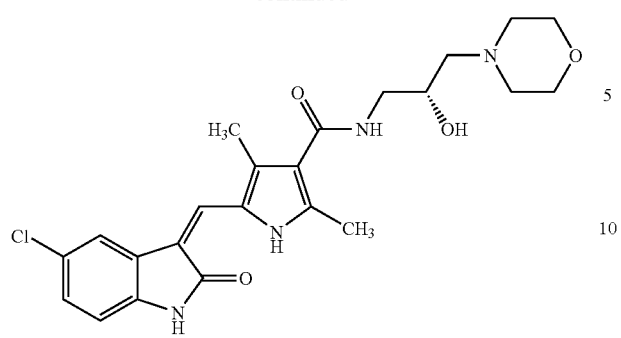
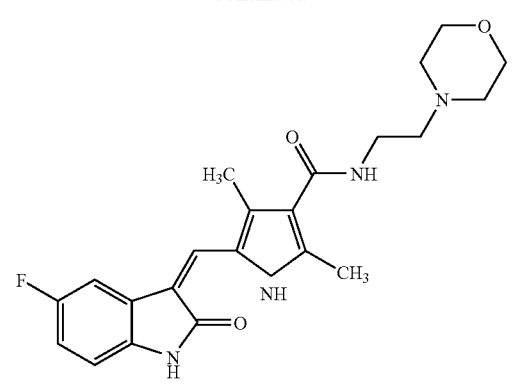
and
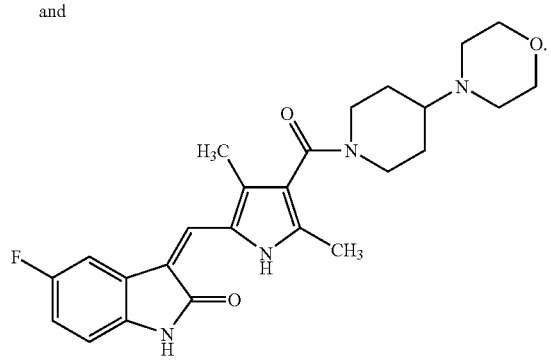
* * * * *